United States Patent [19]

Hall

[11] 4,061,967
[45] Dec. 6, 1977

[54] SUPPORT SYSTEM FOR ROTATABLE DETECTING ELEMENT

[75] Inventor: James R. Hall, Huffman, Tex.

[73] Assignee: Hughes Tool Company, Houston, Tex.

[21] Appl. No.: 756,576

[22] Filed: Jan. 3, 1977

[51] Int. Cl.² .......................................... G01R 33/12
[52] U.S. Cl. .............................. 324/260; 166/65 M; 175/40; 235/449; 340/18 R
[58] Field of Search .................... 324/37, 40, 34 R; 166/65 R, 65 M, 66, 113, 241; 175/40, 45, 220; 346/33 WL, 33 M; 340/18 R, 18 LD, 18 DC; 235/61.11 D

[56] References Cited
U.S. PATENT DOCUMENTS

| 3,066,254 | 11/1962 | Price et al. | 324/37 |
| 3,299,350 | 1/1967 | Tompkins et al. | 324/37 |
| 3,328,681 | 6/1967 | Wood | 324/37 |

Primary Examiner—Robert J. Corcoran
Attorney, Agent, or Firm—Robert A. Felsman

[57] ABSTRACT

An apparatus for supporting a detecting shoe of a sensor for rotation around a drill pipe stem for detecting identification numbers encoded on the drill pipe sections of the stem as they are lowered into a borehole. The apparatus comprises an outer plate means supported for rotation and having an opening in which is located an inner plate also having an opening for receiving the drill stem. Arms couple the inner plate to the outer plate means for rotation therewith and also support the inner plate for lateral movement in the opening of the outer plate means. The detecting shoe is coupled to the inner plate by an arm which moves the shoe against the drill stem for reading purposes. Means also is provided for operating the shoe arm to move the shoe outward to allow drilling or other operations to be carried out.

6 Claims, 10 Drawing Figures

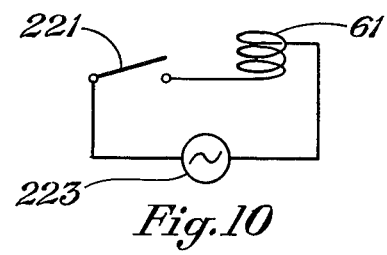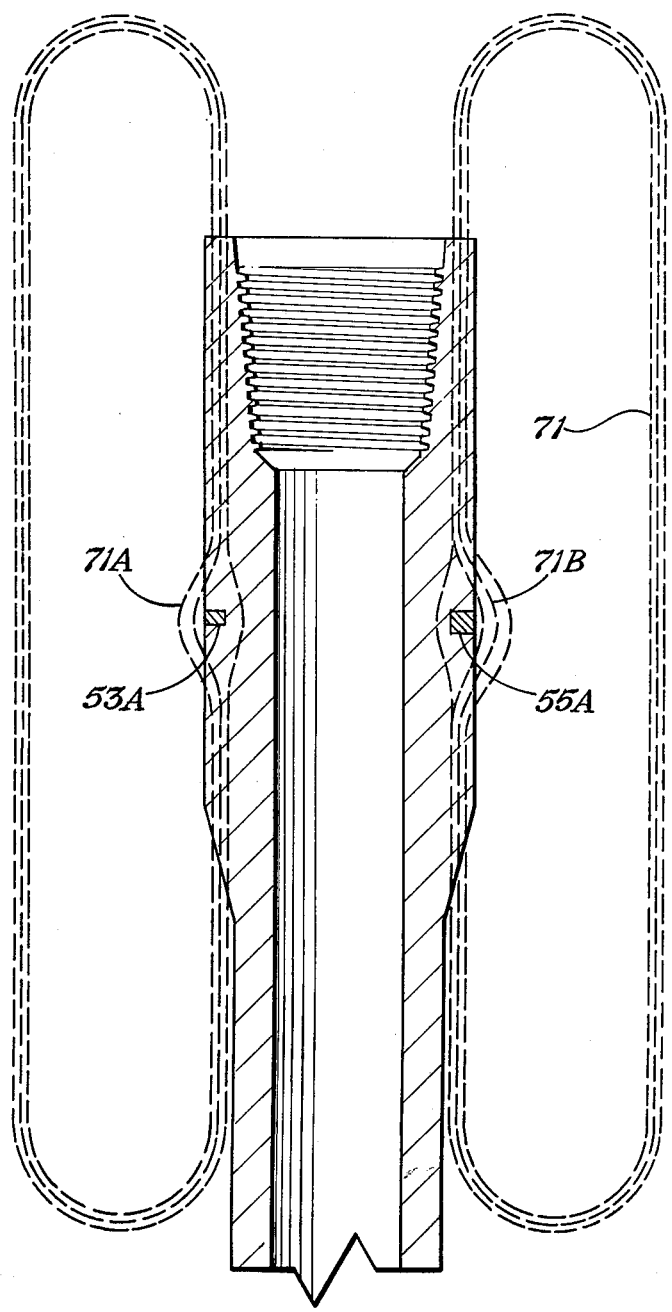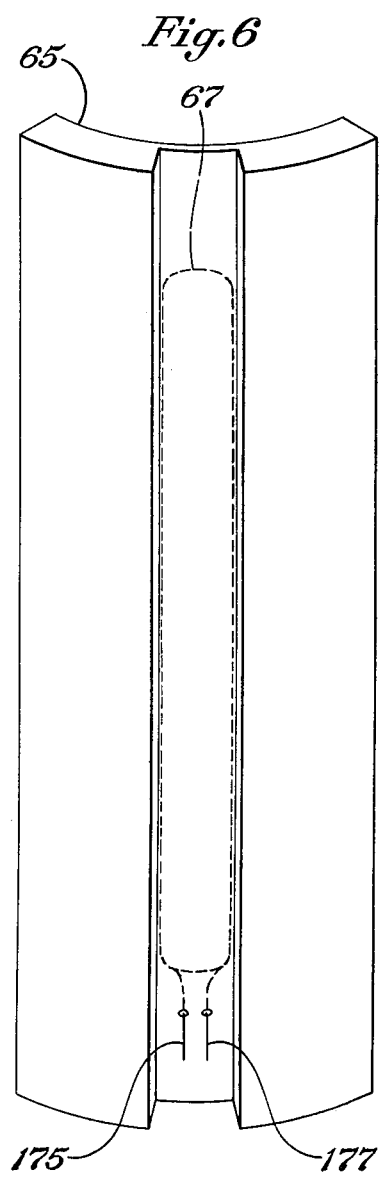

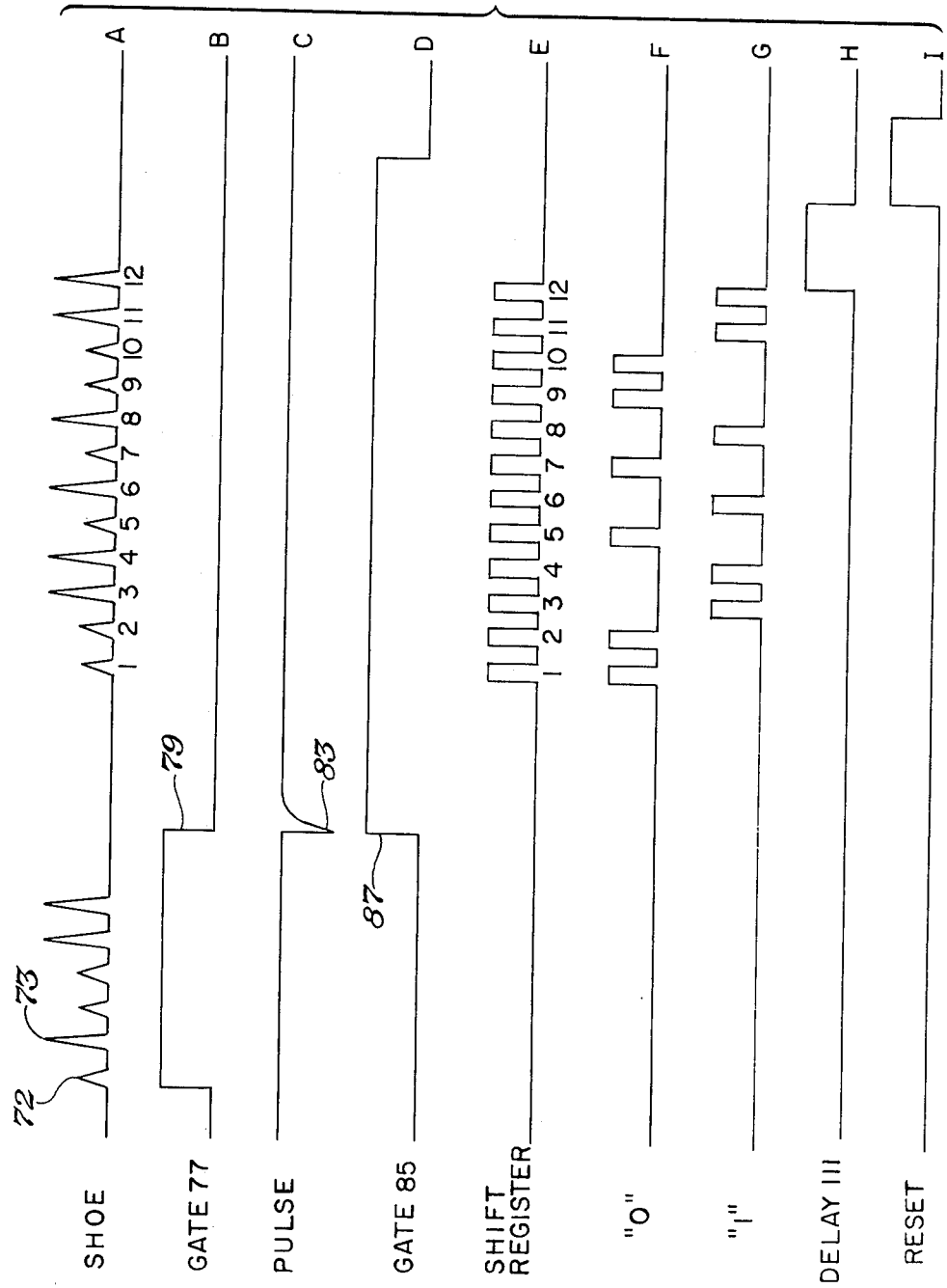

SUPPORT SYSTEM FOR ROTATABLE DETECTING ELEMENT

CROSS-REFERENCES TO RELATED APPLICATIONS

U.S. Patent Application Ser. No. 756,164, entitled DRILL PIPE IDENTIFICATION METHOD AND SYSTEM, filed by Walter A. Gunkel and Robert W. Lybecker on the same date as the present application, U.S. Patent Application Ser. No. 756,215, entitled DRILL PIPE IDENTIFICATION SYSTEM, filed by Edward M. Galle on the same date as the present application.

BACKGROUND OF THE INVENTION

This invention relates to the identification of drill pipe sections employed in a drill string of a borehole drilling system.

In borehole drilling operations, it is desirable to keep track of the position of the drill pipe sections in a drill string and to obtain a record of the service time of each drill pipe section for the purpose of determining fatigue damage. Such information is particularly useful by the contractor in determining the dollar value of the damage occuring to the pipe in drilling a given well and to determine when to downgrade or retire the pipe from service. It is possible to obtain and record this information manually, however, such a technique is time consuming and subject to error.

In a new identification process and system, numbers in binary form, comprising apertures filled with a non-magnetic material, are formed in the outer walls of the drill pipe sections. The numbers are read by a sensor comprising an encircling electrical coil and a detecting element which is rotated around the drill pipe sections as they are moved through the encircling coil.

SUMMARY OF THE INVENTION

It is an object of the present invention to provide an apparatus for use in the above mentioned identification system for supporting the detecting element for rotation around the drill pipe section and which takes into account lateral movement of the drill stem which may occur as it is being lowered into or raised from the borehole.

It is a further object of the present invention to provide an apparatus for supporting the detecting element close to the drill pipe stem during reading operations and which moves the detecting element outward to allow drilling or other operations to be carried out.

The apparatus comprises an outer plate means supported for rotation and having an opening in which is located an inner plate also having an opening for receiving the drill stem. Arms couple the inner plate to the outer plate means for rotation therewith and also support the inner plate for lateral movement in the opening of the outer plate means. The detecting element is coupled to the inner plate by an arm which moves the detecting element close to the drill stem for reading purposes. Means also is provided for operating the detecting element arm to move the detecting element outward to allow drilling or other operations to be carried out.

BRIEF DESCRIPTION OF THE DRAWINGS

FIG. 5 is a cross-sectional view of the end of the drill pipe of FIG. 2 illustrating the magnetic field generated by the encircling electrical coil of the detecting system of FIG. 2;

FIG. 6 is an enlarged view of the detecting element of the detecting system of FIG. 2 which is rotated around the drill pipe sections in the vicinity of the encircling coil;

FIG. 9 are timing diagrams useful in understanding the system of FIG. 8; and

FIG. 10 is an electrical schematic of a system for energizing the encircling electrical coil of FIG. 2.

DRILL PIPE IDENTIFICATION PROCESS AND SYSTEM

Figure 1:
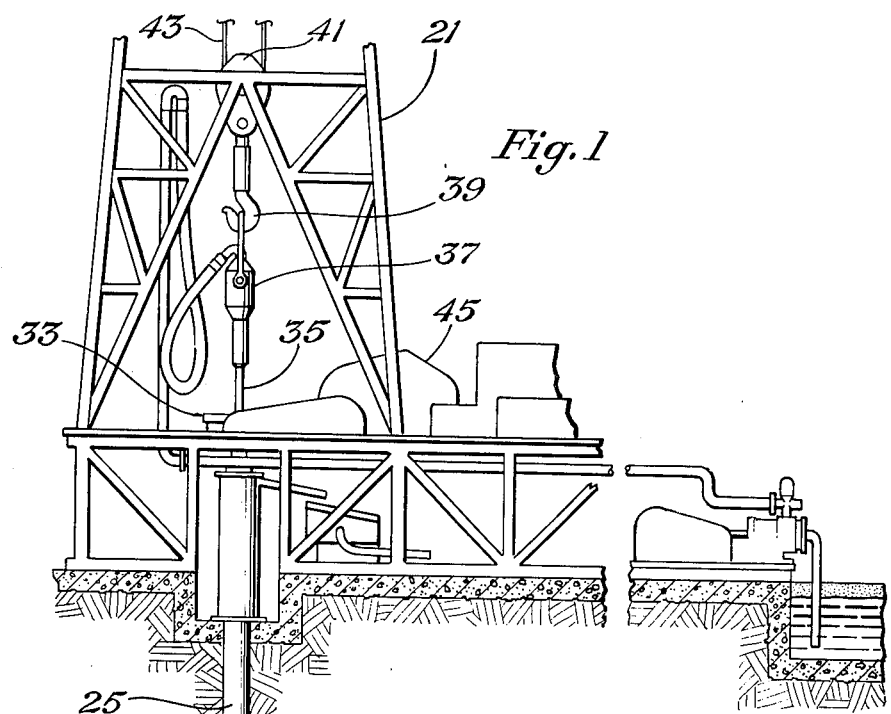
FIG. 1 illustrates a typical borehole drilling system.

Referring to FIG. 1, there is shown a conventional rotary drilling rig. Reference numeral 21 designates a derrick located over a borehole 23 that contains surface casing 25, steel drill pipe sectons 27 threaded together to form a drill string, and a drill bit 31.

The drill pipe sections 27 are threaded together with members commonly called "tool-joints". Such jonts are formed by an externally threaded steel tubular member called a "pin" connected to one end of each pipe section and an internally threaded steel tubular member called a "box" connected to the opposite end of each pipe section. In the drawings, a pin connected to the lower end of a pipe section is identified at 27A and a box connected to the upper end of another pipe section is identified at 27B. These joint members may be connected to the ends of the pipe by welding or by threaded connections.

Rotation of the bit 31 is achieved by the engagement of a rotary table 33 with a kelly 35, which is the upper most tubular member of the drill string. The kelly 35 is attached to a swivel 37 which is supported in the derrick 21 by a hook 39, traveling block 41 and cable 43. The cable 43 is attached through pulleys at the top of the derrick (not shown) to the draw works 45, which lifts and lowers the drill string.

As indicated above, it is desirable to identify and maintain a record of each drill pipe section which is employed as part of the drill string. This is accomplished by encoding an identification number on each drill pipe section and reading the numbers as the drill pipe sections preferably are lowered into the borehole as part of the drill string in preparation for drilling operations. Preferably the numbers are encoded on the box member of each pipe section prior to the attachment of the box to the pipe.

Referring to FIGS. 2–4 and 7, the identification numbers are in binary form and comprise symbols 51 formed on the outer perphery of the box member 27B and hence of the drill pipe section 27. The symbols are of two sizes, a smaller size 53 which represents a "0" binary bit and a larger size 55 which represents a "1" binary bit. The bits are located along a circle defined by the outer periphery of the box member 27B and may comprise 12 bits to provide up to 4,095 different serial or identification numbers.

In forming the bits, 12 holes are drilled into the wall of the box member 27B from the outside in a given plane. The holes extend into the wall a short distance but do not extend through the wall. The 12 holes are equally spaced with respect to each other, except that the spacing between the 12th hole and the 1st hole is greater than the equi-distant spacing between all other holes. They are drilled selectively in one or two diameters, such as one-fourth of an inch and one-eighth of an inch. The smaller diameter holes 53A represent a "0" binary bit and the larger diameter holes 55A represent a "1" binary bit. The holes are plugged or filled with a relatively non-magnetic material 56 having a wear resistance at least equal to that of steel and which preserves a smooth surface on the tool joint member 27B. The plugging material may be for example, stainless steel. Thus, the bits formed by the holes with their non-magnetic inserts have a much lower magnetic permeability than that of the steel walls of the drill pipe. Although 12 bits are disclosed, it is to be understood that more or less than 12 bits may be used to provide more or less than 4,095 different serial numbers.

Figure 2:
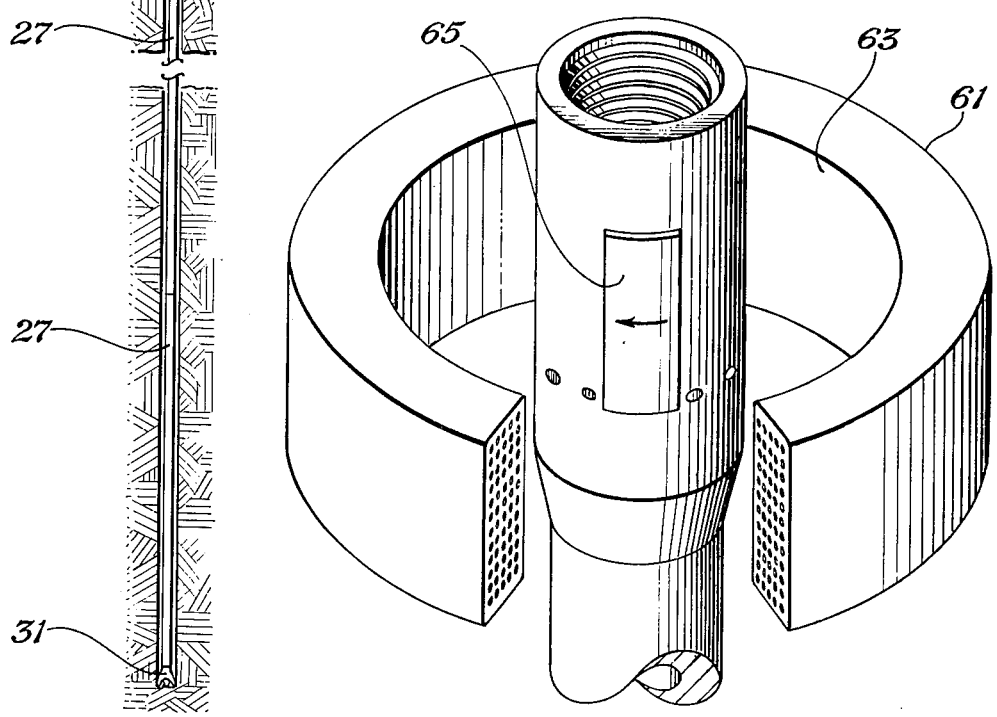
FIG. 2 illustrates an end of a drill pipe identified with a number in binary form and a detecting system comprising an encircling electrical coil and a rotating detecting element for detecting the identification number.

The binary serial number of each individual pipe section may be automatically read as the pipe enters (or leaves) the well by a detecting means or system shown in FIG. 2. This system comprises an electrical coil 61 having an enlarged central opening 63 positioned to receive the drill pipe sections as they are lowered into and raised from the borehole. Also provided is a detecting element 65 which includes a small electrical coil 67 (See FIG. 6) supported to rotate around and in contact with the pipe sections in the vicinity or within the opening 63 of the electrical coil 61. In operation, the electrical coil 61 is energized to generate a magnetic field as illustrated at 71 in FIG. 5. As a pipe section is moved through the coil 61, the magnetic field flows through the wall of the pipe section parallel to the longitudinal axis of the pipe and thus magnetizes the steel pipe. The resulting magnetic flux flows uniformly through the wall of the pipe section except in the area of the encoding holes where a leakage of flux occurs outside of the pipe section because the holes and inserts are non-magnetic and represent an interface to magnetic flux flow. A typical pattern of flux leakage around the holes 53A and 55A is shown at 71A and 71B in FIG. 5.

The shoe 65 is formed of a non-magnetic material such as brass and has the electrical coil 67 embedded therein. As the shoe 65 and hence the coil 67 is rotated in the opening of or within the vicinity of the electrical coil 61, it passes in sequence next to each binary hole as the pipe is moved through the coil 61 and a voltage pulse is induced into the coil 67 by virtue of the coil 67 passing through the magnetic leakage field about each hole. The small diameter holes, representing a "0" bit, induce a voltage pulse into the shoe coil 67 of a particular amplitude and the larger diameter holes, representing a "1" bit, induce a voltage pulse into the coil 67 approximately twice the amplitude of the small hole pulse. Thus, the shoe coil 67 has either a "0" or a "1" amplitude voltage induced into it for each of the holes. The voltage pulses generated thus represent the "0" bits and "1" bits defining a particular binary number encoded on each pipe section. These electrical signals may be removed from the electrical shoe coil 67 by conventional signal retrieval means such as slip rings or FM radio. After retrieval, the signals may be recorded directly on magnetic tape for subsequent analysis and processing. Preferably the signals are processed electronically at the well site to provide a serial number read-out in the desired form. One such circuitry for processing and recording the signals is shown in block diagram in FIG. 8.

Figure 8:
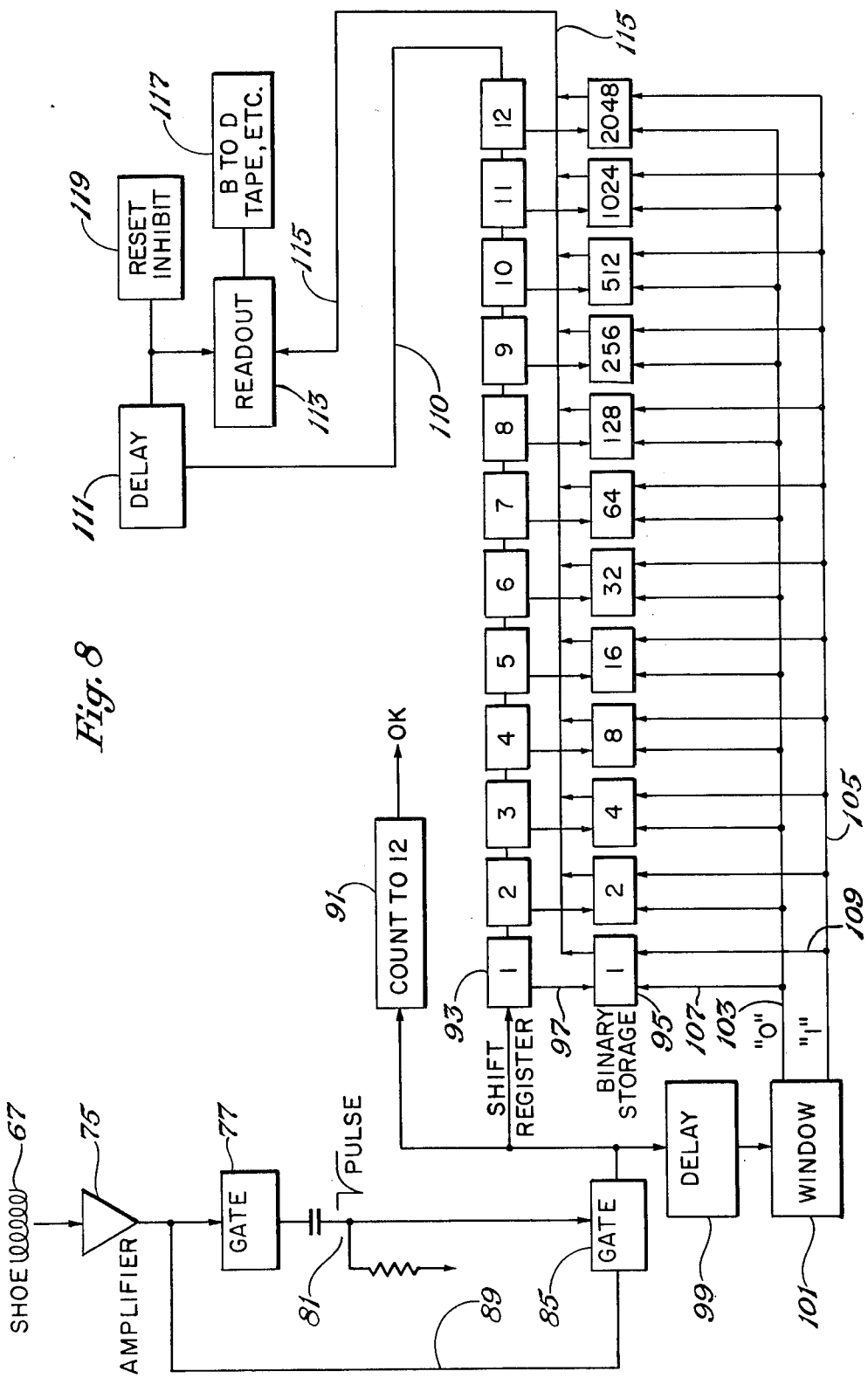
FIG. 8 is an electrical schematic of a system employed for processing and recording the output signals generated by the detecting element of FIG. 6.

Referring now to FIGS. 8 and 9, there will be described the circuitry shown for processing and recording the signals produced by the shoe coil 67. FIG. 9A represents the output of coil 67. The output pulses of the coil 67 occur in two amplitudes 72 and 73 representing "0" and "1" bits. In FIG. 9A, a train of signal pulses are shown at the beginning of the sequence diagram on the left as might occur if the shoe 65 initially comes into the encoded area between the sixth and seventh holes, for example. These six samples do not constitute the full binary count and therefore must be discarded. As seen in FIG. 8, the output of coil 67 is amplified by an amplifier 75. The output of the amplifier 75 actuates a gate 77 which is turned on by the first received pulse from coil 67 and has a time constant long enough to stay on until the next pulse, provided it occurs within the time spacing of the equally spaced holes. The output of the gate 77 is shown in FIG. 9B. After the last signal of the initial train of six signals (or whatever number of signals the initial train has) gate 77 turns off in the absence of an additional signal. A resulting pulse is produced by the gate having a trailing edge 79. The output of gate 77 is differentiated by circuitry 81 to generate a negative pulse when the gate 77 turns off. The negative pulse produced by the circuitry 81 is shown at 83 in FIG. 9C. This pulse turns on a gate 85 whose time constant is set to span the time interval of a full train of twelve pulses which is shown on the right in FIG. 9A. The purpose of this action is to insure that the full series of twelve binary bits are read in sequence. The positive voltage produced by gate 85 is shown at 87 in FIG. 9D. The output of amplifier 75 also is connected to the gate 85 by way of conductor 89. When gate 85 is turned on, it allows the amplified coil signals from amplifier 75 to pass through the gate to a count-to-twelve circuit which, upon counting to twelve and no more or less, activates a circuit to certify that a legitimate reading has occured. The certification circuit may include a light which is turned on for a certain period of time when the exact count-to-twelve has occurred. In addition, the output signals from gate 85 drive a twelve-position shift register 93 and each position of the shift register, in sequence, turns on twelve stages of a binary storage system 95. In this respect, the first pulse from the train of twelve pulses from the shoe 67 turns on the first stage of the shift register 93. The second pulse of the train of twelve pulses from the shoe 67 turns the first stage off, which action turns on the second stage of the shift register 93. The third pulse from twelve pulses from the shoe 67 turns on the third stage of the shift register 93, etc. When a given stage of the shift register is on, the other stages will be off. The outputs of the stages of the shift register 93 are coupled to corresponding stages of the binary storage 95 by way of conductors 97. The output pulses from the twelve stages of the shift register 93 are shown in FIG. 9E.

The output signals from gate 85 also are applied to a delay circuit 99 which delays the signals later in time with respect to the shift register signals. The output of the delay circuit 99 is applied to a window 101 which is in effect a pulse height discriminator. The window 101 differentiates between the low amplitude and the high amplitude signals to generate "0" bit pulses in correct time sequence on conductor 103 and "1" bit signals in correct time sequence on the conductor 105. The signals on conductor 103 are illustrated in FIG. 9F while the signals on conductor 105 are illustrated in FIG. 9G. The time delay of these signals relative to the shift register signals is not illustrated in FIG. 9 because the amount of delay necessary is only about 10 percent of the shift register pulse width and could not be clearly shown in the Figure. The purpose of the time delay is to permit the shift register to fully turn on each binary stage before the application of "0" and "1" bit pulses, in order to be certain the bits are entered uniquely in the correct binary stage. As shown conductor 103 is connected to each stage of the binary storage 95 by way of conductors 107 and conductor 105 is connected to each stage of the binary storage by way of conductors 109. As each of the stages of the shift register 93 are sequentially turned on, each of the stages of the binary storage 95 are sequentially set whereby the binary bit signals on conductors 103 and 105 are appropriately stored in the proper stage of the binary storage 95. Thus, upon shifting to twelve of the shift register 93 the full binary sequence will be stored in the binary storage.

In addition, upon shifting to twelve, the shift register 93 generates a signal which is applied by way of conductor 110 through a delay circuit 111 to activate a read-out circuit 113. The outputs of the twelve stages of the binary storage 95 are connected to the read-out 113 by way of twelve conductors although for purposes of clarity a single conductor 115 is shown. The read-out circuit 113 thus reads the binary numbers stored in the twelve stages of the binary storage and applies them to an appropriate read-out or recording device 117. This device may comprise a binary-to-digital circuit and digital display; a binary-to-digital circuit which is coupled to a tape recorder; a tape recorder for recording the binary data directly on magnetic tape, etc. Simultaneously, the shift to twelve signal applied to delay circuit 111 activates a re-set and inhibit circuit 119 to re-set the shift register and the binary storage stages to zero and to inhibit additional signals from the same pipe section. The connection between the inhibit circuit 119 and the shift register 93 and binary storage 95 are not shown for purposes of clarity. The output of delay circuit 111 is shown in FIG 9H and the output of circuit 119 is shown in FIG. 9I. Additional signals from the same pipe section may be inhibited by applying the output of the inhibit 119 to a circuitry which may be connected to the input of amplifier 75 or of gate 77 to prevent passage, for a predetermined time, of additional pulses from the coil 67 to the circuitry shown.

Circuitry for processing the signals before recording such as that shown in FIG. 8 is preferred since the data recorded is compatible with a computer which may be employed to calculate fatigue damage, cost and other information of the pipe sections. It is not necessary for a computer to be located on the rig, since the data recorded may be processed later through the computer. It is to be understood that circuit arrangements different from that shown in FIG. 8 may be employed to process and record the signals from the shoe coil 67.

DESCRIPTION OF THE PREFERRED EMBODIMENT

Figure 7:
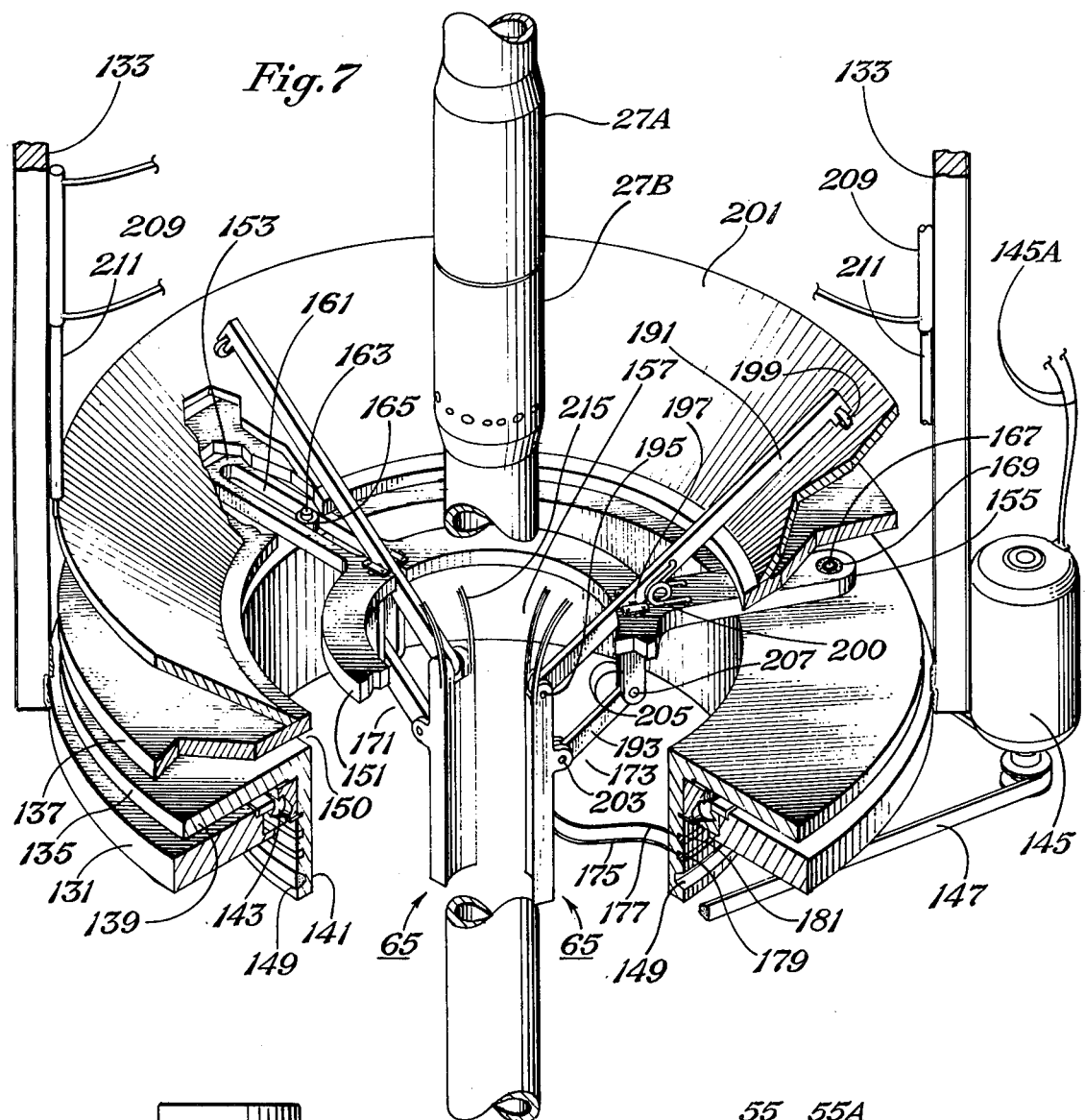
FIG. 7 illustrates the system of the present invention for supporting the detecting element of FIG. 6 for rotation.
Figure 3:
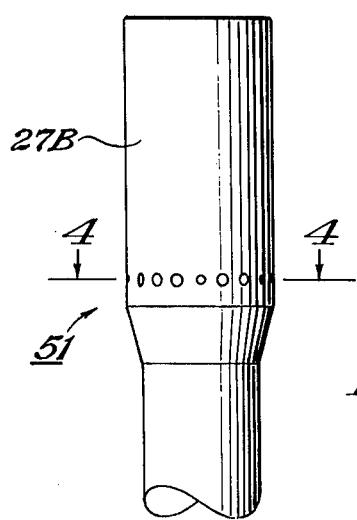
FIG. 3 is a side view of the end of the drill pipe shown in FIG. 2.
Figure 4:
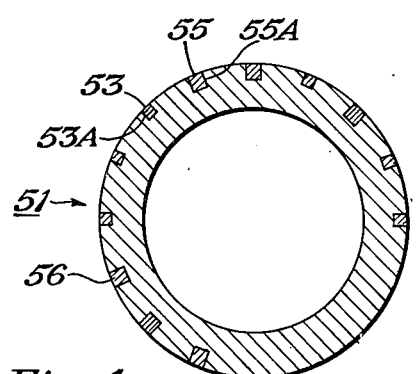
FIG. 4 is a cross-sectional view of FIG. 3 taken along the lines 4—4 thereof.

Referring now to FIG. 7, there will be described the system of the present invention for supporting the detecting shoe 65 and its electrical coil 61 for rotation around the drill pipe sections. The system of FIG. 7 comprises an annular support plate 131 which is fixed to the floor under the rotary table. The central opening of the annular support plate 131 is relatively large and is located to allow the pipe sections to pass through the opening when they are being raised from or lowered into the borehole. The support plate 131 is shown connected to two arms 133 which are in turn connected to the rig to properly locate the support plate. Plate 131 supports two plates 135 and 137 for rotation. Each of plates 135 and 137 is annular in shape and has a central opening slightly less than the opening of the support plate 131. Plate 135 has a horizontal portion 139 and a vertical portion 141 whereby the plate 135 is L-shaped in cross-section. Both of plates 135 and 137 are fixedly connected together (by means not shown) whereby plate 137 is spaced upwardly from plate 135. Bearings 143 support plate 135 and hence plate 137 for rotation relative to support plate 131. The plates are rotated by a motor 145, connected to one of the arms 133, and a belt 147 which fits into a groove 149 formed in the exterior of vertical portion 141 of plate 135.

A smaller diameter plate 151 is supported within the openings of plates 135 and 137. Inner plate 151 is supported by way of three radially extending arms located 120° apart. Only two arms 153 and 155 are shown. These arms ride in the space 150 between the plates 135 and 137 and hence support the plate 151 within the openings of the plates 135 and 137. Plate 151 is annular shaped and has a central opening 157 large enough to receive the drill pipe sections 27 as they are inserted into or removed from the well bore. The openings of plates 135 and 137 are large enough to allow the plate 151 to move laterally therein. Arm 153 has an elongated slot 161 formed therein. A pin 163 is fixedly attached between plates 135 and 137 and is fitted within the slot 161. A roller 165 surrounds the pin 163. Thus, as the outer plates 135 and 137 rotate, the pin 163 and roller 165 fitted within the slot 161 of arm 153 cause the arm 153 and hence the inner plate 151 to rotate with the outer plates as they are rotated by the motor 145 and belt 147. The pin 163 and roller 165 fitted within the slot 161 of the arm 153 also allow the inner plate 151 to translate and pivot about the pin 163 and hence move laterally within the openings of the outer plates 135 and 137 as they rotate. This arrangement allows the inner plate 151 to remain concentric with the drill stem or string as it moves through the opening 157 of the inner plate 151 and in the event that the drill string also moves laterally while moving downward or upward. A bearing 167 is fitted within an aperture 169 of the arm 155 for engagement with the upper surface of plate 135 to allow the arm 155 to move freely. A similar bearing is formed on the outer end of the third arm.

Pivotally attached to the inner plate 151 are three pairs of arms which support three shoes 65 for rotation around the drill pipe sections as they are moved through the opening 157 of inner plate 151. The three pairs of arms are located 120° apart. Only two pairs of arms 171 and 173 supporting two shoes 65 are shown. Three pairs of arms and three shoes are provided for balance purposes. One or two of the shoes may be dummy shoes with the third shoe having the detecting coil 67 embedded therein for reading the binary coded identification numbers on each of the pipe sections as described above. In the alternative, two or all three of the shoes may employ detecting coils 67 to obtain two or three records of the binary coded identification number of each pipe section for comparison purposes to insure accuracy of reading the identification numbers. In FIG. 7, the shoe on the left is a dummy shoe while the shoe on the right has the coil 67 embedded therein for reading the identification numbers. The two ends of the coil 67 are connected to conductors 175 and 177 which in turn are connected to slip rings 179 and 181 supported by the vertical portion 141 of the outer plate 135. Brushes, now shown, are employed to take the signals off of slip rings 179 and 181 and apply the signals by way of conductors to the recording system located on the rig.

Since both paits of arms 171 and 173 are identical and operate in the same manner, only the pair of arms 173 will be described in detail. This pair of arms comprises an elongated arm 191 and a shorter arm 193. Arm 191 has its inner end pivotally connected to the top of the shoe 65 by way of a pivot pin 195. An intermediate portion of the arm 191 is pivotally connected to the inner plate 151 by way of a pivot pin 197. The outer end of the arm 191 has a roller 199 connected thereto and which is adapted to engage an outer beveled plate 201 which has a central opening which coincides with the central openings of plates 135 and 137. As shown the upper surface of plate 201 defines an inverted, hollow, truncated cone. Connected between the arm 191 and the arm 155 of the inner plate 151 is a spring 200 which urges the inner end of arm 191 upward and the outer end of arm 191 downward. The lower arm 193 has its inner end pivotally connected to the shoe 65 by way of a pivot pin 203 and its outer end pivotally connected to two support tabs 205 by way of a pivot pin 207. The tabs 205 are connected to the lower end of the inner plate 151. Two hydraulic cylinders 209, attached to arms 133, have their pistons 211 connected to opposite edges of the plate 201 to move the plate to an upper position or to a lower position.

While the identification numbers of the pipe sections are being read, the beveled plate 201 is located at its lower position where its upward surface is out of engagement with the rollers 199 to allow the pivoting arms 191 urged by the springs 200, to bring the shoes 65 into contact with the drill pipe as it is being lowered into the borehole. Plate 201 is moved to this lower portion by proper actuation of cylinders 209. During reading operations plates 135 and 137 are rotated to rotate the inner plate 151 and its shoe support arms and hence the shoes 65 around the drill pipe. During drillng operations or when large or irregularly shaped pieces are lowered into the borehole, the shoes 65 are retracted to move them outward to allow sufficient space for drilling operations to take place or for large or irregularly shaped pieces to be lowered into the borehole. During this time, rotation of the shoes 65 is terminated. Retraction is accomplished by actuating the cylinders 209 to move the beveled plate 201 upward to engage the rollers 199 to move the outer ends of arms 191 upward which causes the inner ends of the arms 191 and hence the shoes 65 to be moved outward.

Attached to the upper ends of the shoes 65 are flexible guide members 215 for guiding the drill pipe sections through the shoe 65. Although not shown, small rollers may be attached to the inner surfaces of the shoes 65 to reduce their sliding contact with the drill pipe sections and thereby increasing their service life. The components including the inner plate 151 and the shoe supporting arms 191 and 193 may be formed of a non-magnetic material such as brass. The plates 135, 137 and 201 also may be formed of non-magnetic material.

The coil 61 may be supported in place by the support arms 133. It may be located below the plate 131 close to the shoes 65. The shoes 65 and their coils 67 are relatively long and may extend down into the opening of the coil 61 when the shoes 65 are in their reading positions.

Referring to FIG. 10, when it is desired to energize coil 61 for reading purposes, a switch illustrated at 221 will be closed to connect the coil with a source of voltage shown at 223. Although not shown a source of voltage will be connected to the leads 145A of the electric motor 145 with a control switch connected in one of the leads to turn the motor on or off.

In operation, for reading purposes, the cylinders 209 will be actuated to move the plate 201 to its lower position to allow the springs 200 to move the shoes inward against the drill pipe. As the drill pipe is moved through the opening 157 of plate 151, coil 61 will be energized and motor 145 actuated to rotate the shoes 65 around the drill pipe. In order to carry out drilling operations or to lower large pieces of equipment into the borehole, coil 61 will be de-energized and motor 145 stopped to terminate rotation of shoes 65. In addition, cylinders 209 will be actuated to move the plate 201 to its upward position to move the shoes 65 outward.

I claim:

1. A system for use with a detecting means for detecting identification symbols on drill pipe sections as they are moved vertically along a given path of travel by a drilling system employed for carrying out a drilling operations in the earths formations, said detecting means comprising a detecting element to be rotated around the drill pipe sections as they are moved vertically along said path of travel, said system comprising:
   stationary support means,
   outer plate means having an opening for receiving said drill pipe sections as they are moved vertically along said path of travel by said drilling system,
   said outer plate means being supported for rotation by said support means with said opening in line with said given path of travel,
   means for rotating said outer plate means,
   inner plate means having an opening for receiving said drill pipe sections as they are moved vertically along said path of travel by said drilling system,
   the opening of said outer plate means being large enough to receive said inner plate means and to allow said inner plate means to be moved laterally with said opening of said outer plate means,
   coupling means for supporting said inner plate means within said opening of said outer plate means and for coupling said inner plate means to said outer plate means for rotation therewith,
   said coupling means allowing said inner plate means to move laterally relative to said outer plate means and to said support means to allow said inner plate means to remain generally concentric with said drill pipe sections as they are moved through said opening of said inner plate means, and
   attaching means for attaching said detecting element to said inner plate means for rotation therewith and for locating said detecting element close to said drill pipe sections as they are moved through said opening of said inner plate means.

2. The system of claim 1, comprising:
means for engaging said attaching means for moving said detecting element in a direction away from the axis of said opening of said inner plate means.

3. The system of claim 1, comprising:
second outer plate means located close to and above said outer plate means to which said inner plate means is attached, said second outer plate means having an opening in alignment with said opening of said outer plate means to which said inner plate means is attached, said attaching means comprising arm means having an inner end pivotally connected to said detecting element; an intermediate portion pivotally connected to said inner plate means; and an outer end for engaging the upper surface of said second outer plate means, urging means for normally urging the inner end of said arm means upward toward the axis of said opening of said inner plate means, and control means for moving said second outer plate means to upper and lower positions, said second outer plate means when in its lower position allowing the inner end of said arm means and hence said detecting element to be moved by said urging means close to said pipe sections as they are moved through said opening of said inner plate means, said second outer plate means when moved to its upper position having its upper surface in engagement with said outer end of said arm means for moving said inner end of said arm means and hence said detecting element in a direction away from the axis of said opening of said inner plate means.

4. The system of claim 3 wherein:
the upper surface of second outer plate means defines a hollow, inverted, truncated cone, said outer end of said arm means having roller means for engaging the upper surface of said second outer plate means when it is moved to its upper position.

5. The system of claim 1 wherein:
said outer plate means comprises upper and lower plates connected together and spaced vertically from each other, pin means extending between said upper and lower plates, said coupling means comprises a plurality of angularly spaced apart supporting members extending radially outward from said inner plate means and having outer ends located between said upper and lower plates, one of said supporting members having an elongated slot formed therein, said pin means being located in said slot to allow said inner plate means to move toward and away from said pin means and to pivot about said pin means within said opening of said outer plate means.

6. The system of clam 3 wherein:
said outer plate means comprises upper and lower plates connected together and spaced vertically from each other, pin means extending between said upper and lower plates, said coupling means comprises a plurality of angularly spaced apart supporting members extending radially outward from said inner plate means and having outer ends located between said upper and lower plates, one of said supporting members having an elongated slot formed therein, said pin means being located in said slot to allow said inner plate means to move toward and away from said pin means and to pivot about said pin means within said opening of said outer plate means.

* * * * *

UNITED STATES PATENT OFFICE
CERTIFICATE OF CORRECTION

Patent No. 4,061,967          Dated   December 6, 1977

Inventor(s)  James R. Hall

It is certified that error appears in the above-identified patent and that said Letters Patent are hereby corrected as shown below:

Column 2, Line 67, "Perphery" is changed to --Periphery--;
Column 3, Line 14, "one or two" is changed to --one of two--;
Column 6, Line 6, "61" is changed to --67--;
Column 7, Line 15, "Now" is changed to --not--;
Column 7, Line 19, "Paits" is changed to --Pairs--;
Column 7, Line 51, "Portion" is changed to --Position--;
Claim 1, Column 8, Line 56, "With" is changed to --Within--.

Signed and Sealed this

Thirtieth Day of May 1978

[SEAL]

Attest:

RUTH C. MASON
Attesting Officer

LUTRELLE F. PARKER
Acting Commissioner of Patents and Trademarks